United States Patent [19]

Girvin

[11] Patent Number: 5,684,585
[45] Date of Patent: Nov. 4, 1997

[54] OPTICAL PARTICLE COUNTER EMPLOYING A FIELD-CALIBRATOR

[75] Inventor: Kenneth L. Girvin, Grants Pass, Oreg.

[73] Assignee: Met One, Inc., Grants Pass, Oreg.

[21] Appl. No.: 532,900

[22] Filed: Sep. 22, 1995

[51] Int. Cl.⁶ .............. G01J 1/02; G01N 15/02; G01N 21/00
[52] U.S. Cl. ............ 356/336; 356/338; 356/340; 356/243
[58] Field of Search ................ 356/335–338, 356/340, 341, 243

[56] References Cited

U.S. PATENT DOCUMENTS

| | | | |
|---|---|---|---|
| 3,745,455 | 7/1973 | Haigh | 324/71.1 |
| 3,778,617 | 12/1973 | Calhoun | 356/240 |
| 3,867,835 | 2/1975 | Button | 356/243 |
| 3,885,415 | 5/1975 | Burus et al. | 356/243 |
| 4,135,821 | 1/1979 | Pechin et al. | 356/335 |
| 4,434,647 | 3/1984 | Whitcomb et al. | 356/243 |
| 4,613,938 | 9/1986 | Hausen et al. | 356/338 |
| 4,783,599 | 11/1988 | Borden | 356/341 |
| 5,085,500 | 2/1992 | Blesener | 356/338 |
| 5,121,988 | 6/1992 | Blesener et al. | 356/442 |
| 5,373,367 | 12/1994 | DeGunther | 356/337 |

*Primary Examiner*—Frank G. Font
*Assistant Examiner*—Jason D. Vierra-Eisenberg
*Attorney, Agent, or Firm*—Thomas Schneck; George B.F. Yee

[57] ABSTRACT

A particle counter including a modulator to allow electronically determining calibration. The modulator is connected to a driving circuit of a source of light to cause the light to emit a beam of a constant amplitude, representing at least one particle of predefined size. Light transmitted along an optical axis changes in intensity in response to a signal produced by the modulator. A detector is positioned to sense the change in intensity to produce signals proportional to the light sensed. A displaying device, such as a pulse height analyzer, is in electrical communication to receive the signals produced by the detector to quantitatively display the change in intensity of the light.

19 Claims, 4 Drawing Sheets

OUTPUT PULSE

OPTICAL PARTICLE COUNTER EMPLOYING A FIELD-CALIBRATOR

TECHNICAL FIELD

The present invention pertains to systems for optically detecting, sizing and counting particulate matter in a fluid stream, commonly referred to as particle detectors. Specifically, the present invention pertains to a device for calibrating particle detectors.

BACKGROUND ART

Particle detectors have been used for a variety of purposes to detect the presence and/or size of particles in various fluids, including air and other gases, as well as liquids, such as water, hydraulic oils and lubricants. They have proved particularly useful to control contamination in many industrial environments. For example, particulate contamination can cause hydraulic equipment and the like to fail due to excessive accumulation of particles in the hydraulic fluid. Even though filters are used in such equipment to continuously remove particles, the filters may become clogged and may rupture due to excess pressure build-up across the filter membrane. Also, microelectronic fabrication requires a "clean room" in which particulate contaminants, e.g., dust, are filtered from an atmosphere of a room. The filters used in "clean rooms" are also subject to clogging and compromise, resulting in particulates entering a "clean room" atmosphere in great quantities. Failure to provide a "clean room" results in particulate contamination of the devices during fabrication which reduces yield. Particle detectors are thus used in such environments to detect particles in specified size classes and report the cleanliness level of the fluid according to categories specified by industry standards.

There are two basic designs for a particle detector. One design detects particles using scattering light techniques, and the other detects particles using light extinction techniques. FIG. 1 shows a typical prior art particle detector employing light scattering techniques and includes a light source 11 optically coupled to a lens 13, which defines an optical axis 15. Disposed coaxially with the optical axis 15, opposite to the light source 11, is a light trap 17. Lying along the optical axis 15 between the light source 11 and the light trap 17 is a view volume 19. The light source 11 directs a beam 21 along the optical axis 15 through a fluid flow passing through the view volume 19. Particles present in the fluid flow scatter and absorb a portion of the light energy. The scattered light diverges from the optical axis 15. The scattered light 23 is collected by a detector 25 positioned off the optical axis 15. The detector 25 produces electrical signals corresponding to the light detected. The signals may be digitized and displayed accordingly. In this manner, a determination is made concerning the size and number of particles in each size class which are present in the fluid flow. An example of a particle counter employing light scattering techniques is disclosed in U.S. Pat. No. 5,085,500 to Blesener.

FIG. 2 shows a typical prior art particle detector employing light extinction techniques. Similar to the particle detector of FIG. 1, an extinction particle detector includes a light source 27 optically coupled to a lens 29, which defines an optical axis 31. Unlike scattering particle detectors, a detector 33 is disposed coaxially with the optical axis 31, opposite to the light source 27. Lying along the optical axis 31 between the light source 27 and the detector 33 is a view volume 35. The light source 27 directs a beam 37 along the optical axis 31 through a fluid flow passing through the view volume 35. The lens 29 defines a focal point in the view volume 35 so that particles present in the fluid flow attenuates the light energy sensed by detector 33. The detector 33 produces electrical signals corresponding to the light sensed, which may be digitized and displayed accordingly. Although less sensitive than particle detectors employing light scattering techniques, particle detectors employing light extinction techniques are more suitable for detecting particles in liquids. An example of a particle counter employing light extinction techniques is disclosed in U.S. Pat. No. 5,121,988 to Blesener et al.

In order for these particle detectors to provide an accurate measure of a sample's level of cleanliness, they must be periodically calibrated. Further, the periodicity of calibration should be frequent to ensure proper operation of the particle detector. One primary calibration technique of a light scattering particle counter includes passing a sample of spherical beads of known sized repeatedly through the particle counter to obtain sufficient data points for adequate statistical analysis.

U.S. Pat No. 4,135,821 to Pechin et al. discloses a primary calibration technique for particle counters employing light extinction techniques including a disc disposed in the view volume. The disc includes a plurality of opaque radially extending wires. The wires are disposed to sweep across the path of a beam of light as the disc rotates about an axis. A detector is positioned to sense the reduced light transmission resulting from the wires blocking the light path. In this manner, the wires represent particles of known sizes. As mentioned above, a number of data points are obtained to provide a statistically significant sample of measurements which are used to determine the calibration of the particle detector.

U.S. Pat. No. 4,434,647 to Whitcomb et al. discloses a calibration system used for the primary calibration of particle detectors which detect and size particles present in fluids. The system includes a probe which carries a spot of a known size. The probe has a cross-section typically smaller than the view volume and includes an oscillator to allow movement into and out of the view volume. The spot is made to pass through a light beam present in the view volume. A sensing unit detects a change in light intensity and produces an electrical pulse in proportion to the change in the light intensity sensed. A drawback with the aforementioned calibration system is that it requires exactingly positioning the probe within the view volume, requiring fine adjustment of precision equipment which can be easily misaligned.

Other drawbacks with the prior art primary calibration techniques for particle detectors is that the primary calibration procedure itself is time-consuming and requires special equipment not typically present in the field, i.e., environment where particulate detection is required. Often the end-user of a particle counter does not have the equipment necessary to properly check calibration. Typically, the end-user contracts with the vendor of the particle counter to perform primary calibration procedures. This often necessitates moving the particle counter from the field and shipping it back to a vendor's laboratory for calibration, resulting in significant operational down-time for the particle counter. In addition, due to the time consuming procedures required for calibration, the periodicity of the primary calibration is often infrequent, resulting in an increased possibility that a particle counter is not providing accurate data regarding the particulate contamination in a given environment.

It is an object, therefore, of the present invention to provide a particle counter employing a calibration device for use in the field.

It is a further object of the present invention to provide a device for rapidly determining the operational characteristics of a particle counter.

SUMMARY OF THE INVENTION

These objects have been achieved with a particle counter including a modulator to electronically vary the intensity of a beam. The intensity may be periodically varied in accord with a predetermined frequency, or the intensity may be varied once to a constant level for a fixed duration of time. The modulator is connected to modulate the signal of a driving circuit of a source of light of the particle counter to vary the beam intensity so that light sensed by a detector simulates the beam impinging upon a particle of predetermined size. The modulator includes a memory device which stores the amplitude and width of the pulses necessary to modulate the drive signal accordingly. Light transmitted along an optical axis of a particle counter into a view volume periodically changes intensity in response to a signal produced by the modulator. The detector is positioned to sense the change in intensity in the view volume, and the detector produces signals proportional to the light sensed. A displaying device, such as a pulse height analyzer, is in electrical communication to receive the signals produced by the detector to quantitatively display the change in intensity of the light. In one embodiment, the detector is coaxial with the optical axis, and the modulator attenuates the beam intensity. In a second embodiment, the modulator signal increases the intensity of light emitted by the light source. In this manner, a detector positioned off the optical axis senses the variation of intensity of the light emitted. With the aforementioned features, a secondary calibration method is provided which allows quickly determining the calibration of a particle counter without the need to remove it from the field.

BEST MODE FOR CARRYING OUT THE INVENTION

Figure 1:
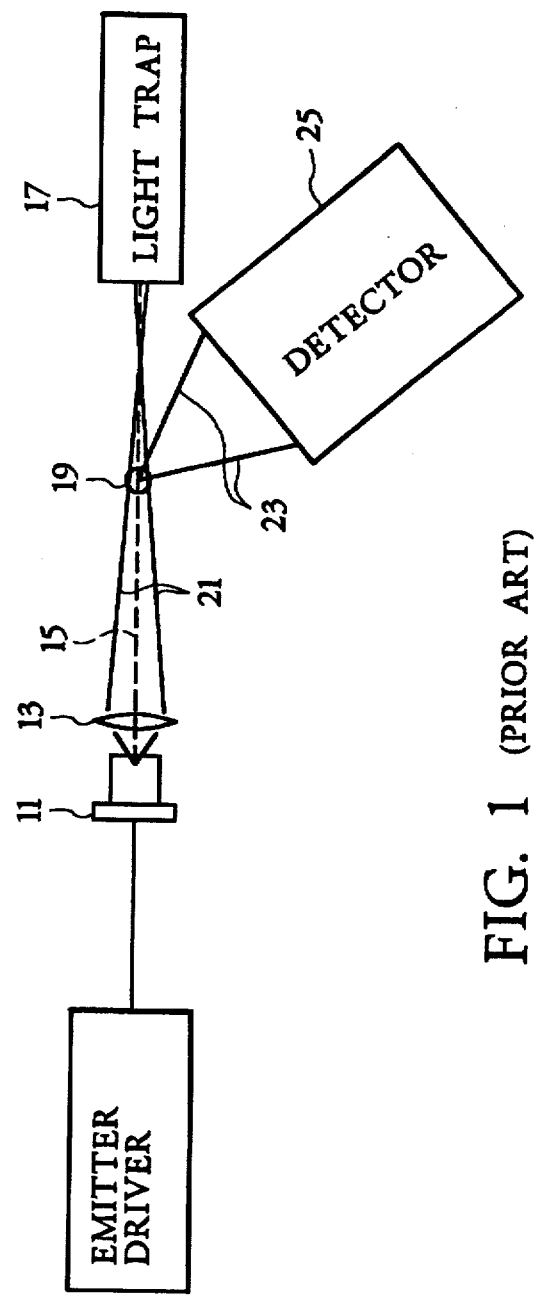
FIG. 1 is a simplified plan view of a particle detector of the prior art employing light scattering techniques.
Figure 2:
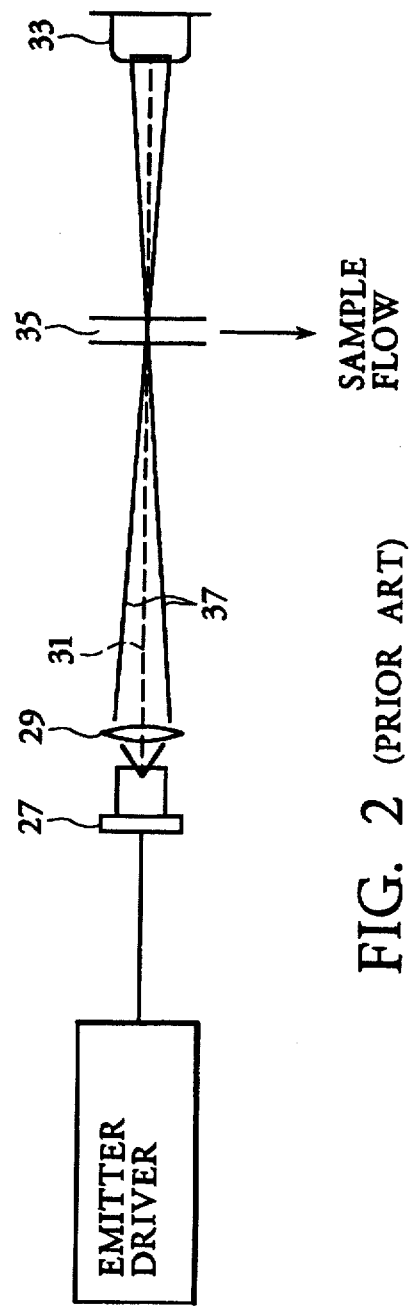
FIG. 2 is a simplified plan view of a particle detector of the prior art employing light extinction techniques.
Figure 3:
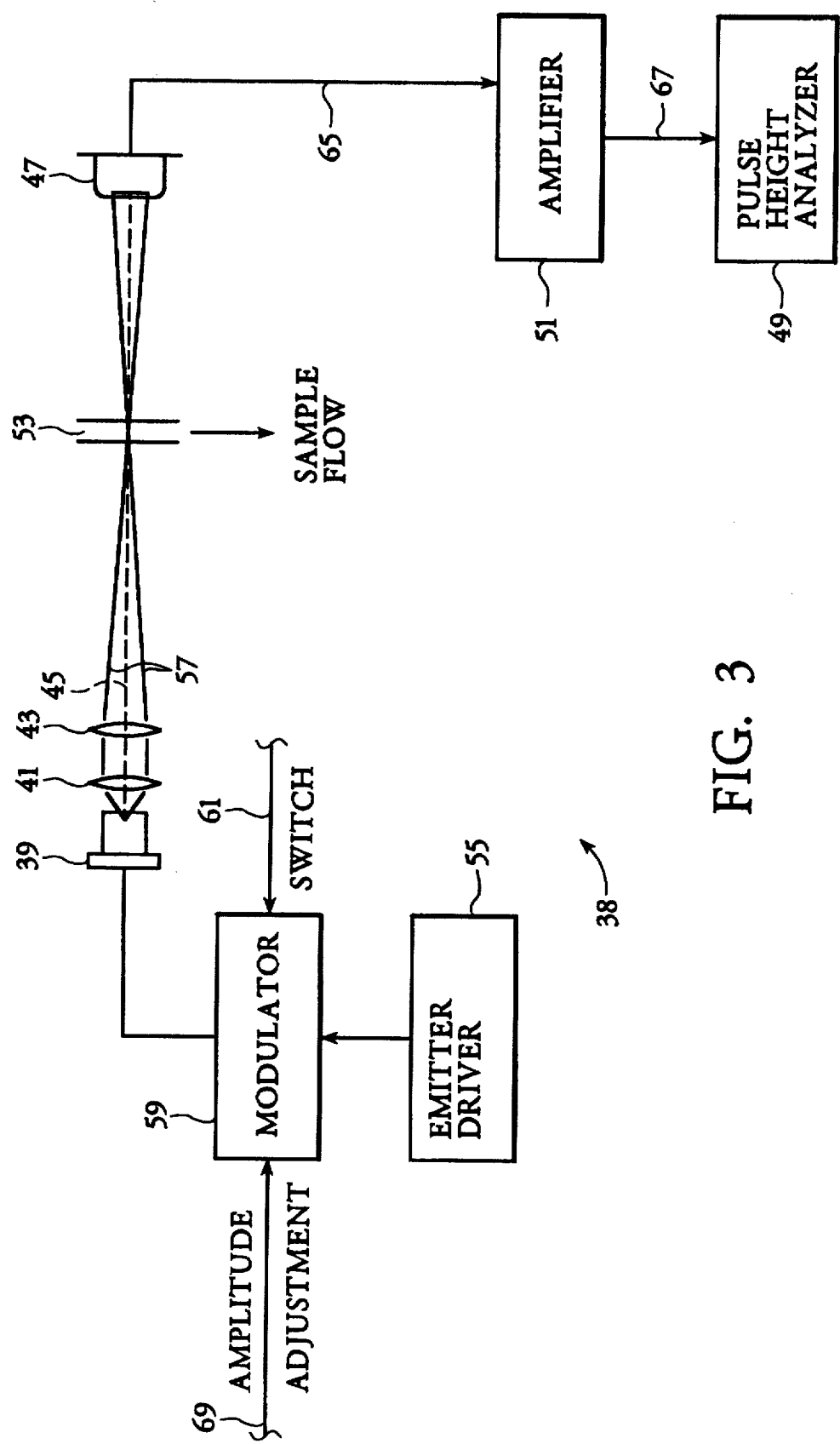
FIG. 3 is a simplified plan view of a particle counter employing light extinction techniques in accord with the present invention.

FIG. 3 shows the preferred embodiment of a particle counter 38 in accord with the present invention. The particle counter 38 employs light extinction techniques and includes a light source 39 optically coupled to beam shaping optics 41 and 43, which define an optical axis 45. Disposed coaxially with the optical axis 45, opposite to the light source 39, is a detector 47. The detector is in electrical communication with a pulse height analyzer 49 via an amplifier 51. Lying along the optical axis 45 between the light source 39 and the detector 47 is a view volume 53. An emitter driver 55 is in electrical communication with the light source 39 which directs a beam 57 along the optical axis 45 through a fluid flow, such as a gas or liquid, passing through the view volume 53. Electrically connected between the emitter driver 55 and the light source 39 is a modulator 59.

Figure 4:
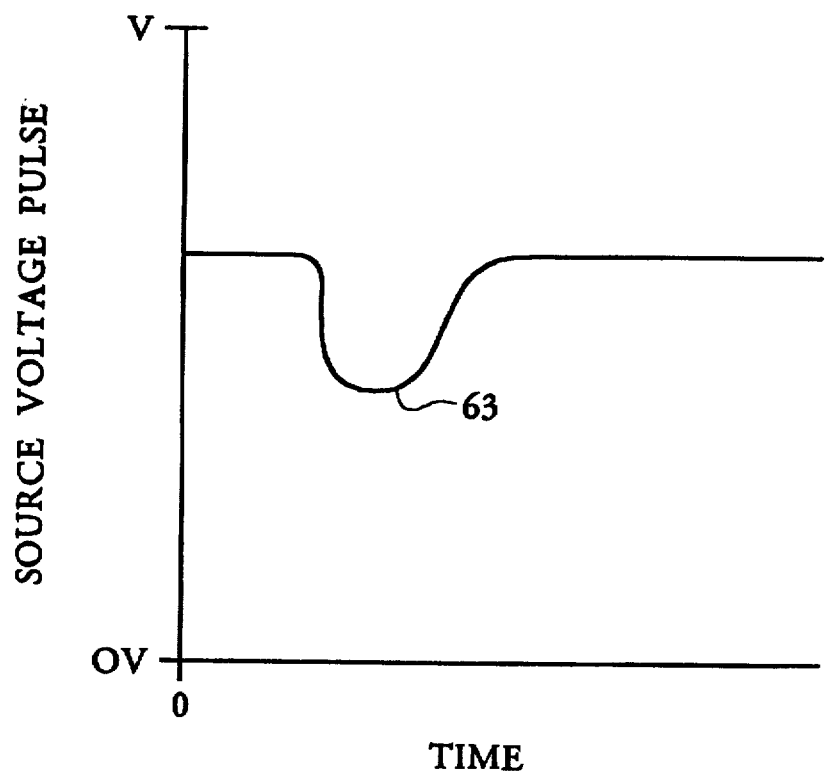
FIG. 4 is a graph of time versus voltage showing a pulse produced in accord with the present invention.
Figure 5:
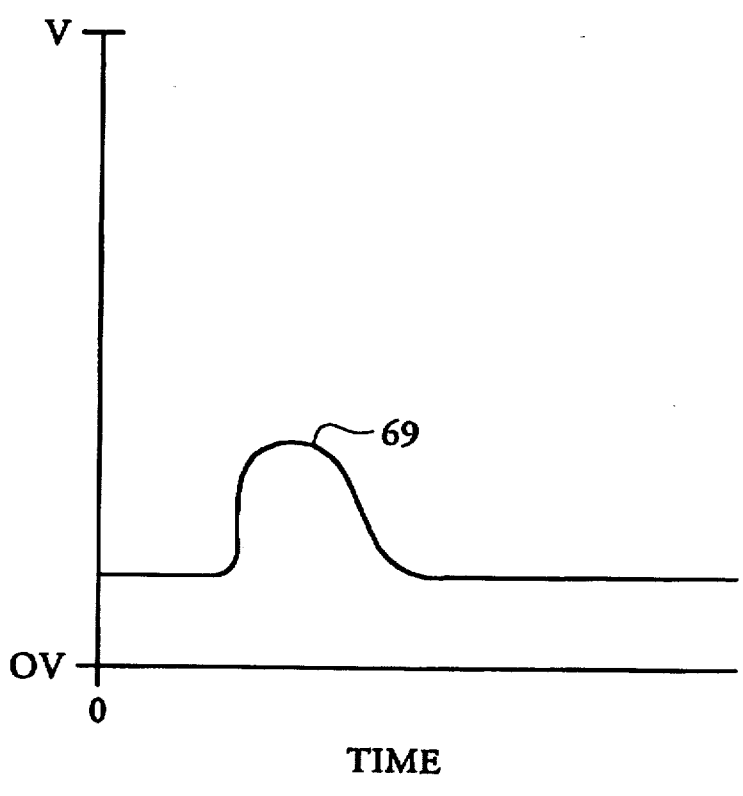
FIG. 5 is a graph of time versus voltage representing a change in light sensed by a detector of the particle counter shown in FIG. 3.

To determine whether the particle counter 38 is accurately detecting and sizing particulate matter in a fluid flow, the emitter driver 55 produces a signal that causes the light source 39 to emit the beam of light 57 with a predefined intensity. The modulator 59 is activated, via switch 61, either manually or electronically, to produce a modulated drive signal 63 as shown in FIG. 4. A plurality of modulated signals 63 may be produced to cause the light source 39 to periodically vary the intensity of the beam at a predetermined frequency, or a single signal 63 may be produced to vary the intensity once for a predetermined duration of time. As the particle counter 38 employs light extinction techniques, the modulated signal 63 attenuates the beam 53's intensity. The detector 47 senses the change in the beam 53's intensity and produces signals proportional to the light sensed. Signal conditioning circuitry, such as amplifier 51, is connected to receive the signals from the detector 47 over line 65. A displaying device, such as a pulse height analyzer 49, is connected to receive the signals from the amplifier 51 over line 67 to display the signals as an output pulse 69, as shown in FIG. 5. The amplitude and width of the output pulse 69 may be compared to a predefined value to determine whether the counter is properly calibrated. This comparison may be performed either manually or automatically by transmitting the output signal 69 to a processing unit, not shown.

Although any type of light source may be employed, typically light source 39 is a laser emitting a beam having a wavelength ranging from 750 to 850 nm. The modulator 59 may be adjusted to emit a signal that will periodically vary the intensity of the beam 57 emitted by the light source at a predetermined frequency so that the light sensed by the detector 47 represents a plurality of particles of predetermined size moving in a fluid flow. Alternatively, the modulator 59 may be adjusted to emit a signal that will vary the intensity of the beam 57 once for a predetermined duration of time so that the light sensed by the detector 47 represents a single particle of predetermined size moving in a fluid flow. Typically, the signals produced by the detector 47 are proportional to a corresponding signal of at least one particle having a size in the range of 1 to 120 microns; although, the intensity of the beam 57 may be varied to represent any particle size within the dynamic range of the detector 7. Adjustments to the modulator 59 are made by the amplitude adjustment switch 69, which is typically set during the primary calibration for the particle counter 38. In this fashion, the amplitude adjustment switch operates as a memory device, storing the requisite pulse amplitude and pulse width necessary to vary the beam intensity accordingly. The adjustments to the modulator may be set using any of the calibration methods of the prior art. One such calibration method is described in U.S. Pat. No. 4,434,647 to Whitcomb et al. which is incorporated by reference.

In operation, it is preferred that the modulator 59 produce a plurality of modulated signals so that the light sensed by the detector 47 represents a plurality of particles of predetermined size moving in a fluid flow. The particle counter 38 is set to 50% counting efficiency so that it will only detect half of the beam intensity variations per unit of time. For example, if the modulator 59 were to produce 100 signals 63 per minute, the counter 38 would be set so that only 50 intensity variations would be detected in the same unit of time. Detecting more than or less than 50 beam variations could signify that the particle counter 38 was in need of primary calibration or repair. A reduction in the number of intensity variations sensed could indicate that the detector 47 may be dirty or the light source 39 degrading. Conversely, if the detector 47 sensed an increase in the number of intensity variations, this could also signify malfunctioning of the counter 38. Without the use of the modulator, malfunctioning of the counter 38 would not be observed until primary calibration was attempted or catastrophic failure of the counter was observed.

Figure 6:
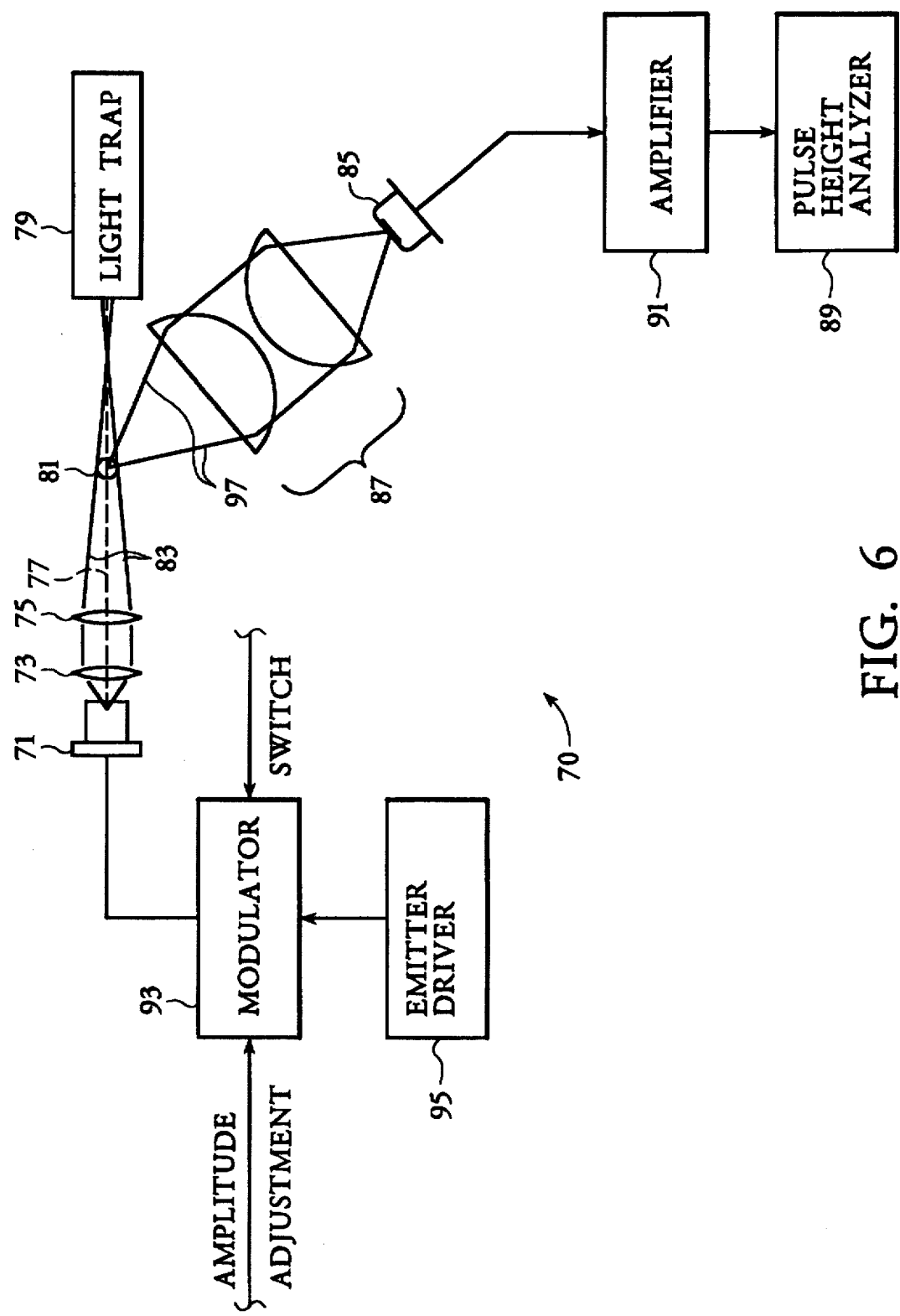
FIG. 6 is a simplified plan view of a particle counter employing light scattering techniques in accord with the present invention.

FIG. 6 shows another embodiment of the present invention employed in a particle counter using light scattering techniques. In this embodiment, a light source 71 is optically coupled to beam shaping optics 73 and 75 which define an optical axis 77. Disposed coaxially with the optical axis 77, opposite to the light source 71, is a light trap 79. Lying along the optical axis 77 between the light source 71 and the light trap 79 is a view volume 81. The light source 71 directs a beam 83 along the optical axis 77 into a fluid flow passing through the view volume 81. A detector 85 is located off the optical axis 77 and is in optical communication with the view volume 81 via a collection lens assembly 87. The detector 85 is in electrical communication with a pulse height analyzer 89 via an amplifier 91. Similar to the embodiment discussed above with respect to FIGS. 3–5, the present embodiment includes a modulator 93, an emitter driver 95 and the light source 71 driven by the emitter driver 95.

As discussed above with respect to FIGS. 3–5, to determine whether the particle counter 70 is accurately detecting and sizing particles present in a fluid flow, the emitter driver 95 produces a signal that causes the light source 71 to emit the beam of light 83 with a predefined intensity. The modulator 93 is activated, as discussed above with respect to FIGS. 3–5, to produce a modulated drive signal. The modulated signal causes the light source 71 to change the intensity of the beam to a predetermined level, either periodically or once for a predetermined duration of time. As the particle counter 70 employs light scattering techniques, the modulated signal typically increases the beam 83's intensity so that a portion 97 of the beam 83 is collected by lens assembly 87. The intensity of the beam 83 may be increased for a given duration of time so that the portion 97 collected by the lens assembly 87, and sensed by the detector 79, may represent a particle of any size moving in a fluid flow. Preferably, the beam intensity is increased, to a predetermined level, periodically to represent a plurality of particles moving in a fluid flow. Typically, the particle size represented will be in the range of 0.3 to 10 microns. The detector 85 senses the change in the beam 83's intensity by detecting the portion 97 of the beam 93 collected by the lens assembly 87. The detector 85 produces signals proportional to the light sensed. These signals are then conditioned and displayed as discussed above.

The advantages of the present invention is that it provides a secondary calibration procedure that is less time-consuming than the primary calibration procedures of the prior art. The present invention provides an electronic calibration check which abrogates the need to provide additional equipment which requires precise alignment, and, at times, removal of the particle counter from the field/end-user's locale. This permits frequent calibration checks of a particle counter which ensures that accurate particle measurements are made, facilitating compliance with strict standards being promulgated by various industries.

I claim:

1. A continuous flow particle counter, of the type wherein a sample fluid is passed through a beam of light, with the beam impinging on particles suspended in the sample fluid, the particle counter comprising:

a source of light to generate said beam;

a modulator having means for adjusting the intensity of said beam in a manner to simulate the detection of a particle of known size; and a detecting means for sensing the intensity of said beam and producing a signal corresponding to the size of a detected particle;

said modulator further including means, coupled to receive said signal, for quantitatively displaying said intensity sensed.

2. The particle counter as recited in claim 1 wherein said modulator attenuates the intensity of said beam to simulate extinction of light by at least one particle of predetermined size.

3. The particle counter as recited in claim 1 wherein said modulator amplifies the intensity of said beam to simulate scattering of light by at least one particle of predetermined size.

4. The particle counter as recited in claim 1 wherein said beam is directed along an axis with said source and said detector co-axially disposed along said axis.

5. The particle counter as recited in claim 1 wherein said beam is directed along an axis with said source and said detector disposed to receive light diverging from said axis.

6. The particle counter as recited in claim 1 wherein said modulator further includes control means for adjusting the intensity of said beam to simulate the detection of a plurality of particles of known sizes.

7. The particle counter as recited in claim 6 wherein said modulator further includes means for storing information relating to sizes of said plurality of particles, said means for storing being coupled to provide said information to said control means.

8. A continuous flow particle counter, of the type wherein a sample fluid is passed through a beam of light, with the beam impinging on particles suspended in the sample fluid, the particle counter comprising:

a source of light to generate said beam;

memory means for storing information corresponding to a particle of predetermined size;

a modulator means, coupled to said memory means, for selectively varying the intensity of said beam in accord with information stored in said memory means in a manner to simulate detection of a particle of a size corresponding to said stored information;

a detecting means for sensing the intensity of said beam and producing signals proportional to the sizes of detected particles; and means, coupled to receive said signals, for quantitatively displaying said intensity sensed.

9. The particle counter as recited in claim 8 wherein said source of light includes an emitter driver producing a driving signal to drive said source to emit a beam having a predetermined intensity, said modulator means in electrical communication with said emitter driver to modulate said driving signal to vary the intensity of said beam for a predetermined duration of time.

10. The particle counter as recited in claim 10 wherein said displaying means is a pulse height analyzer.

11. The particle counter as recited in claim 10 wherein said displaying means includes an amplifier in electrical communication with both said detecting means and said pulse height analyzer.

12. The particle counter as recited in claim 9 further including a lens assembly in optical communication with said detecting means to focus light onto said detecting means.

13. The particle counter as recited in claim 12 wherein said beam is directed along an axis with said source and said detecting means co-axially disposed along said axis.

14. The particle counter as recited in claim 13 wherein said modulator means amplifies the intensity of said beam to simulate scattering of light by particles of predetermined size.

15. The particle counter as recited in claim 12 wherein said beam is directed along an axis with said source and said detecting means disposed to receive light diverging from said axis.

16. The particle counter as recited in claim 15 wherein said modulator means attenuates the intensity of said beam to simulate extinction of light by particles of predetermined size.

17. A method for calibrating a continuous flow particle counter, of the type wherein a sample fluid is passed through a beam of light, with the beam impinging on particles suspended in the sample fluid, the method comprising:

providing information relating to the size of a particle;

producing said beam of light at a first intensity;

simulating detection of said particle, including (i) adjusting the intensity of said beam of light from said first intensity to a second intensity, said second intensity based on said information and (ii) performing said step of adjusting at specified intervals of time;

detecting a change in the intensity of said beam of light;

producing signals proportional to the change of intensity detected, with said signals corresponding to known signals from particles of predetermined size; and comparing said signals against said information to determine whether said particle counter is in calibration, said step of comparing being performed at said specified intervals of time.

18. The method as recited in claim 17 wherein said changing step includes increasing the intensity of said beam.

19. The method as recited in claim 17 wherein said changing step includes the step of attenuating the intensity of said beam.

* * * * *

UNITED STATES PATENT AND TRADEMARK OFFICE
CERTIFICATE OF CORRECTION

PATENT NO. : 5,684,585
DATED : November 4, 1997
INVENTOR(S) : Kenneth L. Girvin

It is certified that error appears in the above-identified patent and that said Letters Patent is hereby corrected as shown below:

Column 4, line 50, "detector 7" should read - - detector 47 - -.

Claim 10, column 6, line 64, "as recited in claim 10" should read - - as recited in claim 9 - -.

Signed and Sealed this

Tenth Day of March, 1998

Attest:

BRUCE LEHMAN

Attesting Officer

Commissioner of Patents and Trademarks